United States Patent [19]

Moked et al.

[11] 4,452,956

[45] Jun. 5, 1984

[54] DISCRETE SPIRAL FLOW IMPARTING DEVICE

[75] Inventors: Isaac Moked, New Brunswick; Richard H. Handwerk, South Somerville, both of N.J.; Hans J. Goettler, Fargo, N. Dak.

[73] Assignee: Union Carbide Corporation, Danbury, Conn.

[21] Appl. No.: 234,204

[22] Filed: Feb. 13, 1981

Related U.S. Application Data

[62] Division of Ser. No. 93,016, Nov. 9, 1979, Pat. No. 4,284,105.

[51] Int. Cl.³ .............................................. C08F 2/02
[52] U.S. Cl. ........................................ 526/64; 526/88
[58] Field of Search ..................................... 526/64, 88

[56] References Cited

U.S. PATENT DOCUMENTS

| | | | |
|---|---|---|---|
| 4,000,357 | 12/1976 | Marano | 526/64 |
| 4,007,321 | 2/1977 | Scholz | 526/64 |
| 4,076,919 | 2/1978 | Urban | 526/64 |
| 4,168,355 | 9/1979 | Sonoda | 526/64 |
| 4,209,599 | 6/1980 | Brady | 526/64 |

*Primary Examiner*—Paul R. Michl
*Attorney, Agent, or Firm*—Clement J. Vicari

[57] ABSTRACT

Apparatus for imparting spiral motion to material flowing in a tube comprising a relatively short spiral member anchored to prevent movement relative to said tube, said spiral member having maximum length shorter than said tube, said spiral member capable of imparting spiral motion to the entire amount of material flowing in said tube.

4 Claims, 1 Drawing Figure

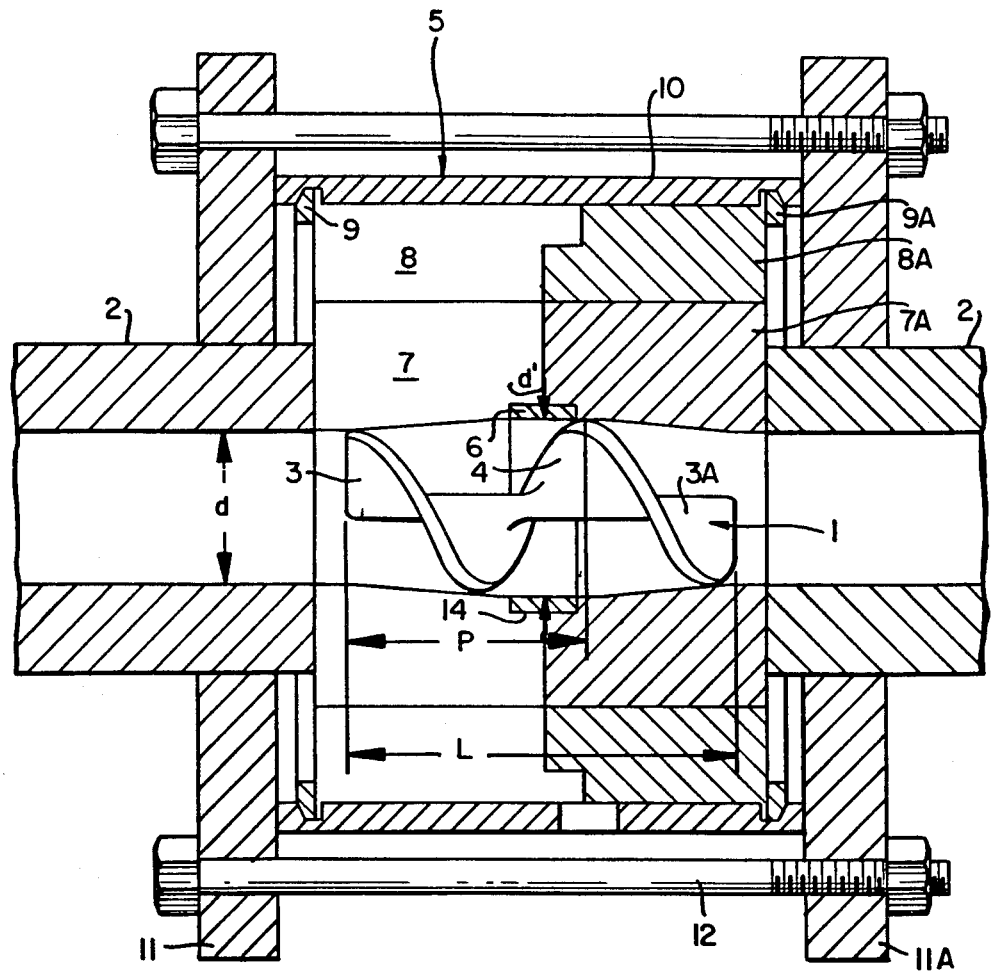

DISCRETE SPIRAL FLOW IMPARTING DEVICE

This application is a division of our prior U.S. application Ser. No. 093,016, filing date 11/09/79, now U.S. Pat. No. 4,284,105.

BACKGROUND

This invention relates to improving the heat transfer to or from materials flowing in a tube. A typical application for this invention is the high-pressure polymerization of olefins in presence of free-radical-generating initiators in a tubular reactor comprising a series of discrete tubes connected in series.

When materials of high viscosity, such as partially polymerized ethylene, flow through an elongated tubular polymerization reactor, it is difficult to transfer heat to or from them. This difficulty is believed to be caused by fouling of the tube walls with layers of material. A method of improving heat transfer by imparting spiral motion to at least part of the material flowing in the tube is disclosed by U.S. application No. 093,017, filed of even date herewith and now abandoned, content of which is incorporated herein by reference. However, it is difficult to inexpensively construct means for imparting spiral motion capable of withstanding the very high forces exerted by materials flowing at high pressure differentials. Furthermore, the force of material flowing past spiral-motion-imparting devices tends to move the devices downstream relative to the tube, away from their original location.

Other difficulties encountered with spiral-flow-imparting device installed within a tube are:

(a) it is not easy to install and remove the devices, which may be necessary to obtain optimum reactor performance under different conditions;

(b) such devices are relatively expensive;

(c) such devices may become part of the tube and, therefore, need to be replaced every time the tube is replaced.

(d) such devices are adversely affected by irregularities in the tube such as eccentricity, varying diameter and lack of straightness;

(e) such devices may be subject to deformation during installation, and, therefore, are incapable of imparting spiral motion in a desired predetermined pattern.

OBJECTS

Accordingly, it is an object of this invention to provide apparatus for imparting spiral motion capable of withstanding the force of very viscous material flowing by it in a tube at high pressure differentials.

It is another object of this invention to provide apparatus for imparting spiral motion to material flowing in tubes wherein the apparatus will not move downstream with the flowing material.

It is a further object of this invention to provide a process for polymerizing olefins that achieves greater heat transfer than plain-bore tubular reactors.

It is yet another object of this invention to provide relatively inexpensive apparatus for imparting spiral motion that is capable of rapid installation and removal as a modular unit.

It is still another object of this invention to provide apparatus for imparting spiral motion to material flowing in tubes such that the apparatus will out-last the tubes.

It is still a further object of this invention to provide apparatus for imparting spiral motion to material flowing in tubes that allows the motion to be predetermined, and that is not affected by irregularities in the tube.

Another object of this invention is to provide apparatus capable of imparting various degrees of spiral motion at different regions along a tubular reactor.

SUMMARY OF THE INVENTION

These and other objects are achieved by the present invention, one aspect of which comprises:

Apparatus for imparting spiral motion to material flowing in a tube comprising a relatively short spiral member anchored to prevent movement relative to said tube, said spiral member having maximum length shorter than said tube, said spiral member capable of imparting spiral motion to the entire amount of material flowing in said tube.

A second aspect of the invention comprises:

A process for manufacturing polyolefin or copolymers of olefin containing up to 60 mole percent of other polymerizable monomer comprising:

(a) supplying monomer at pressure of at least 15,000 psig to an inlet of a tubular reactor having a length to diameter ratio of at least 500 to 1;

(b) polymerizing said monomer in presence of free-radical-generating initiator at temperature of at least 100° C.;

(c) imparting spiral motion to material flowing through said reactor by flowing the material past a spiral member, said spiral member having maximum length shorter than said tube; and (d) removing polymer and unpolymerized monomer from an outlet of said reactor.

A third aspect of the invention comprises:

Apparatus for installation at a joint of two tubes for imparting spiral motion to material flowing in said tubes comprising:

(a) a spiral member having two ends and a central portion, wherein said central portion has diameter exceeding that of said ends;

(b) a hollow housing snugly fitting over said spiral member, said housing comprising:
 a ring to fit snugly around the central portion of said spiral member,
 mating blocks having tapered openings for said spiral member and a seat for said ring, and
 means for holding said mating blocks in contact with each other.

U.S. application Ser. No. 093,017, filed of even date herewith and now abandoned, discloses use of a twisted tape as a method of imparting spiral flow to materials flowing in a tube. However, that application contemplates installation of relatively long twisted tapes within the reactor tubes. As stated previously, spiral-flow-imparting devices, such as twisted tapes, installed inside of tubes are subject to several difficulties. This invention is predicated on the finding that imparting spiral motion to the entire amount of material flowing through a tube over a relatively short length causes a surprising increase in the overall heat transfer coefficient that persists for a very long time after the material has flowed past the spiral-motion-imparting device. By installing the relatively short spiral-motion-imparting devices of this invention as modular units at tube joints of a polymerization reactor many advantages are attained:

(1) The devices are easy to install and remove, allowing ability to adapt to changing reactor conditions caused by, for example, changing products.

(2) The devices are relatively inexpensive to install and remove.

(3) The devices do not become part of the reactor tubing, and hence do not need to be replaced on the relatively frequent occasions when reactor tubing must be replaced.

(4) The performance of the devices is not adversely affected by irregularities in the reactor tubing.

(5) The devices do not change shape during installation, hence they are capable of imparting predetermined spiral motion.

(6) By installing devices of varying configuration, varying degrees of spiral motion may be imparted at different regions along the reactor.

IN THE DRAWING

The sole FIGURE illustrates a spiral flow imparting device constructed in accordance with the invention.

DETAILED DESCRIPTION OF THE INVENTION

In the drawing, material to or from which it is desired to obtain better heat transfer is flowing in tube 2. In order to impart spiral motion, spiral member 1 has been placed in the flow path. Spiral member 1, is constructed somewhat in the form of a helix to impart spiral motion to the entire amount of material flowing in the tube. Preferably the spiral motion will be imparted so as to rotate the material at least 360° about the axis of the tube. Spiral member 1 has length 1 shorter than the tube, and preferably no longer than 20 tube inner diameters. More preferably length 1 will be about 2 to 6 tube inner diameters. Preferably the pitch p will be $\frac{1}{2}$ to 10 times inner diameter d. To prevent its movement relative to the tube, spiral member 1 must be anchored, preferably by installing it at a joint in the tubing. More preferably the spiral member is anchored within a modular member capable of attachment to the tube at a joint. This can be accomplished by the construction illustrated.

In the drawing, spiral member 1 has ends 3 and 3A, and central position 4. The diameter d' of central portion 4 exceeds that of ends 3 and 3A, which in this case is equal to that of tube 2. Spiral member 1 fits snugly within housing 5.

A convenient method of constructing housing 5 is to have it comprise: ring 6, which fits snugly over central portion 4; mating blocks 7 and 7A, having tapered openings for the spiral member and seat 5 for ring 6; and means for holding the mating blocks in contact with each other. Here mating blocks 7 and 7A are held together by outer housing rings 8 and 8A, retaining rings 9 and 9A and sleeve 10. The tubing joint is closed by flanges 11 and 11A and bolt 12. Other closures are acceptable.

Of course other methods of anchoring the spiral member to prevent movement relative to the tubes are acceptable.

It is emphasized that the discrete spiral-flow-imparting devices of the present invention are capable of increasing the amount of heat transferred to or from material flowing in the tube for long distances downstream of the devices itself. Hence, if more than one device is installed, it is preferable to install the devices no closer to each other than 50 tube inner diameters, and more preferably no closer than 100 tube inner diameters.

Of course helices having more than one lead, i.e. double, triple or higher helices, may be used.

A preferred application for this invention is in the manufacture of polyolefin or copolymer of olefin containing up to 60 mole percent of other polymerizable monomer, such as ethyl acrylate, vinyl acetate, butyl acrylate, carbon monoxide or acrylic acid. The monomers are supplied at pressure of at least 15,000 psig to an inlet of a tubular reactor having a length to diameter ratio of at least 500 to 1 and polymerized in presence of free-radical-generating initiator and possibly chain transfer agent, both of which are well known to those skilled in the art. After polymerization has taken place at temperature of at least 100° C., polymer and unpolymerized monomer are removed from an outlet of the reactor.

Spiral motion may be imparted to material flowing in the reactor by installing devices constructed in accordance with the invention at tube joints, possibly throughout the entire reactor, or at least at the place where maximum temperature is reached and/or toward the end of the reactor to lower the reactor outlet temperature. Conditions within existing reactor and desirable properties of the polymer produced may govern. For example, if the peak temperature can be no higher than present, installing these devices near the place where the peak is reached will allow use of more initiator which will bring about higher amounts of conversion of monomer to polymer within the reactor. Optionally, it may be desirable to feed side streams of additional initiator at different points. Those skilled in the art and familiar with individual reactors and conditions therein will be able to modify operating conditions to achieve better results with the invention.

EXAMPLE I

Spiral flow imparting devices constructed in accordance with the FIGURE were installed in an elongated tubular ethylene polymerization reactor having inside diameter d of 1 inch. Spiral member 1 was made of TZM, an alloy containing 99.25 percent molybdenum, 0.55 percent titanium, 0.12 percent zirconium and trace amounts of other elements. Housing 5 was made of 15-5 PH stainless steel. Pitch P was 1$\frac{1}{2}$" and central portion diameter d' was 1$\frac{1}{8}$". The helix had 1$\frac{3}{4}$ turns.

Monomer was fed to the reactor at rates of 16,000 to 21,000 lb/hr during the test. The spiral flow imparting devices were installed at 12 foot intervals for a section of the reactor.

The inside heat transfer coefficient for the entire 12 feet of reactor length downstream of the spiral flow imparting devices increased by a factor of 1.05 to 1.5 over the average recorded for bare tubes in the same section of this reactor. Since this type of reactor does not reach true steady state, the inside heat transfer coefficient is not constant, hence the spread between the factor by which that coefficient was increased. However, it is believed that the average inside heat transfer coefficient attained by practicing this invention is close to 1.5 times that attained with a bore tube. This is a truly remarkable improvement considering that it was imparted to a 12 foot length of tubing by a device less than 3 inches long.

The devices remained inside the tubular reactor for several days without any problems. However, after that time, some decompositions, inevitable in this type of reaction occurred. These decompositions caused some of the helical members to slide relative to their housings and move slightly down stream. It is believed that a machining error resulting in a tapered angle in mating blocks 7 and 7A smaller than specified was at least partially responsible for this failure. However, it may be desirable to take some corrective measures on future installations. For example, spiral member 1 could be welded to ring 6, or it may be desirable to make the ratio of central portion diameter d' to end diameter d larger.

EXAMPLE II

Fluids of viscosity between roughly 3 and 20 cp were pumped through a 12' length of pipe at Reynolds number between about 2,000 to 14,000. The pipe had an inside diameter of 1". Helices constructed in accordance with the table were installed at the beginning of the 12' run through the plain bore pipe. The resulting increase in inside heat transfer coefficient ($H_i$) and pressure drop ($\Delta p$) are shown in the table.

TABLE

| Helix No. | d | d' | p | l | Root Diameter[1] | Increase in $h_i$ | Increase in $\Delta p$ |
|---|---|---|---|---|---|---|---|
| 1 | 1" | 1⅛" | 1½" | 2⅝" | 0.170 | 1.4–1.6 | 2.8–3.2 |
| 2 | 1" | 1⅜" | 1½" | 2⅝" | 0.375 | 1.3–1.5 | 4.0–5.0 |
| 3 | 1" | 1⅜" | 1¾" | 3 3/16" | 0.400 | 1.0–1.1 | 3.8–4.1 |
| 4 | 1" | 1⅜" | 2" | 3½" | 0.375 | 1.0–1.1 | 3.2–3.8 |

[1]Root diameter is the diameter of the stem passing through the longitudinal axis of the helix.

As indicated by the table, a large increase in $h_i$ over a long length can be attained by using a very short helix in accordance with the present invention. The extra $\Delta p$ caused by the helix will be acceptable in many cases.

Surprisingly, data indicate that the extra pressure drop caused by the devices does not significantly increase when the Reynolds number is increased.

What is claimed is:

1. A process for manufacturing polyolefin or copolymers of olefin containing up to 60 mole percent of other polymerizable monomer comprising:
   (a) supplying monomer at pressure of at least 15,000 psig to an inlet of a tubular reactor having a length to diameter ratio of at least 500 to 1 and containing a tube in said reactor;
   (b) polymerizing said monomer in presence of free-radical-generating initiator at temperature of at least 100° C.;
   (c) imparting spiral motion to material flowing through said reactor by flowing the material past a spiral member, said spiral member having maximum length shorter than said tube; and
   (d) removing polymer and unpolymerized monomer from an outlet of said reactor.

2. The presence of claim 1 wherein said polyolefin is polyethylene.

3. The process of claim 2 wherein said other polymerizable monomer is selected from the group consisting of ethyl acrylate, vinyl acetate, butyl acrylate, carbon monoxide and acrylic acid.

4. The process of claim 1 wherein said step (c) spiral motion is imparted by flowing material past at least two spiral members having at least two different configurations located in different regions in the reactor.

* * * * *